US008216611B2

(12) United States Patent
Caron et al.

(10) Patent No.: US 8,216,611 B2
(45) Date of Patent: Jul. 10, 2012

(54) COMBINED-STEP PROCESS FOR PHARMACEUTICAL COMPOSITIONS

(75) Inventors: David A. Caron, Natanya (IL); Lina Al-Bargash, Laguna Beach, CA (US)

(73) Assignee: Mylan Pharmaceuticals ULC, Etobicoke, Ontario (CA)

( * ) Notice: Subject to any disclaimer, the term of this patent is extended or adjusted under 35 U.S.C. 154(b) by 835 days.

(21) Appl. No.: 11/910,434

(22) PCT Filed: Mar. 30, 2006

(86) PCT No.: PCT/CA2006/000470
§ 371 (c)(1),
(2), (4) Date: Oct. 24, 2008

(87) PCT Pub. No.: WO2006/102750
PCT Pub. Date: Oct. 5, 2006

(65) Prior Publication Data
US 2009/0074854 A1     Mar. 19, 2009

(30) Foreign Application Priority Data

Mar. 30, 2005   (CA) .................................... 2505463

(51) Int. Cl.
*A61K 9/14*   (2006.01)
(52) U.S. Cl. .................... 424/489; 424/451; 424/464
(58) Field of Classification Search .................. None
See application file for complete search history.

(56) References Cited

U.S. PATENT DOCUMENTS

| 4,696,943 A | 9/1987 | Gobert et al. |
| 4,837,223 A | 6/1989 | Gobert et al. |
| 4,943,639 A | 7/1990 | Gobert et al. |
| 5,204,115 A * | 4/1993 | Olinger et al. ............. 424/470 |
| 2003/0185891 A1 * | 10/2003 | Crew et al. ............... 424/486 |
| 2003/0215504 A1 * | 11/2003 | Upadhyay et al. .......... 424/465 |
| 2005/0267222 A1 * | 12/2005 | Iwata et al. .............. 514/698 |

FOREIGN PATENT DOCUMENTS

| EP | 0162036 B1 | 8/1989 |
| WO | 0139779 A1 | 6/2001 |
| WO | 03101428 A1 | 12/2003 |
| WO | 2004069796 A2 | 8/2004 |
| WO | 2004100992 A2 | 11/2004 |
| WO | 2006080029 A1 | 8/2006 |
| WO | 2006123357 A2 | 11/2006 |

OTHER PUBLICATIONS

Abberger, The effect of powder type, free moisture and deformation behaviour of granules on the kinetics of fluid-bed granulation, European Journal of Pharmaceutics and Biopharmaceutics, 2001, p. 327-336, vol. 52, Elsevier, Amsterdam, Netherlands.
Adam et al., Factors Influencing Capping and Cracking of Mefenamic Acid Tablets, Drug Development and Industrial Pharmacy, 2000, p. 489-497, vol. 26 (5), Informa Healthcare, New York, N.Y., U.S.A.
Faure et al., Process control and scale-up of pharmaceutical wet granulation processes: a review, European Journal of Pharmaceutics and Biopharmaceutics, 2001, p. 269-277, vol. 52, Elsevier Science Publishers B.V., Amsterdam, Netherlands.
Hausman, Comparison of Low Shear, High Shear, and Fluid Bed Granulation During Low Dose Tablet Process Development, Drug Development and Industrial Pharmacy, 2004, p. 259-266, vol. 30 (3), Informa Healthcare, New York, N.Y., U.S.A.
Laohavichien et al., Effect of Binders, Disintegrants and Their Interactions on Fluidized Bed Produced Tablet Characteristics, Pharmazeutische Industrie, 2000, p. 992-998, vol. 62 (12), Cantor, Aulendorf, Germany.
Nouh, The Effect of Variations in Concentration and Type of Binder on the Physical Characteristics of Sulfadiazine Tablets and Granulations Prepared by Wet and Fluidised-Bed Granulation Method, Pharmazeutische Industrie, 1986, p. 670-673, vol. 48 (6), Cantor, Aulendorf, Germany.
Wan et al., Fluidized Bed Granulation with PVP K90 and PVP K120, Drug Development and Industrial Pharmacy, 1995, p. 857-862, vol. 21 (7), Informa Healthcare, New York, N.Y., U.S.A.
Slangen, Simultaneous Granulation and Drying of Filter Cake, Chemical Engineering & Technology, Nov. 20, 2002, p. 1193-1196, vol. 25 (12), Wiley InterScience, San Francisco, CA, U.S.A.
Summons to attend oral proceedings in corresponding EP Patent Application No. 06741364.1, issued Mar. 25, 2011.
Makino, T., "New challenges for granulation technology: design and super scale-up of fluidized-bed granulation for tablet manufacturing," J. Jpn. Soc. Pharm. Mach. & Eng., 14(1) 5-15, 2005 (English Abstract Only).
Japanese Office Action dated Feb. 14, 2012.

* cited by examiner

*Primary Examiner* — Bethany Barham
(74) *Attorney, Agent, or Firm* — Janine A. Moderson; Amin Talati, LLC

(57) ABSTRACT

The invention relates to a process for the solid oral pharmaceutical formulation of a pharmaceutically active ingredient such as levetiracetam, comprising a wet granulation of the pharmaceutically active ingredient and simultaneous fluid bed drying such that, as the pharmaceutical blend granulates it is simultaneously dried thus preventing it from becoming a paste. The invention therein thus provides a novel formulation preparation process characterized by a "combined" Granulation and Fluid Bed Drying process step.

15 Claims, No Drawings

COMBINED-STEP PROCESS FOR PHARMACEUTICAL COMPOSITIONS

CROSS REFERENCE TO RELATED APPLICATIONS

This application claims the benefit of priority under 35 USC §365(c) of International Application No. PCT/CA2006/000470, with an international filing date of Mar. 30, 2006, which claims priority to Canadian patent application number 2,505,463, filed Mar. 30, 2005, which are incorporated herein by reference in their entirety.

FIELD OF THE INVENTION

The present invention relates to a novel process for the preparation of a pharmaceutical composition.

BACKGROUND OF THE INVENTION

Drug substances most frequently are administered orally by means of solid dosage forms such as tablets and capsule. Tablets may be defined as solid pharmaceutical dosage forms containing drug substances with or without suitable diluents and prepared either by compression or moulding methods. Compressed tablets usually are prepared by large-scale production methods. These tablets are formed by compression and contain no special coating. They are made from powdered, crystalline or granular materials, alone or in combination with excipients.

The most widely used and most general method of granulation used in tablet and capsule manufacture is the wet-granulation method. Its popularity is due to the greater probability that the granulation will meet all the physical requirements for the compression of good tablets. When tablet or capsule ingredients are sensitive to moisture or are unable to withstand elevated temperatures during drying, and when the tablet or capsule ingredients have sufficient inherent binding or cohesive properties, slugging may be used to form granules. This method is also referred to as dry granulation. For tablets in which the drug itself constitutes a major portion of the total tablet weight, it is necessary that the drug possess physical characteristics required for the formulation to be compressed directly. Direct Compression consists of compressing tablets directly from powdered material without modifying the physical nature of the material itself. Other related granulation processes include spheronization, spray-drying and spray congealing. The round beads in spheronization allow for better flow of material. The uniform size and spherical shape resulting material in spray-drying also improves flowability. While spray congealing allows formulators to use material best suited for adapting to prolonged release forms of the drug (Remington: The Science and Practice of Pharmacy, 19$^{th}$ Ed. Vol. II).

Levetiracetam of formula (I):

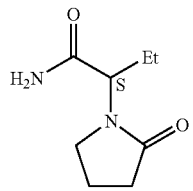

or (−)-(S)-α-ethyl-2-oxo-1-pyrrolidine acetamide is an anticonvulsant drug and its therapeutic uses are disclosed, for example, in U.S. Pat. No. 6,903,130, U.S. Pat. No. 4,943,639 and U.S. Pat. No. 4,696,943. For example, levetiracetam is useful for the treatment of motion sickness, hyperkinesia, hypertonia, convulsive disorders, such as epilepsy, memory disorders, hypoxic and ischemic type aggressions of the CNS, bipolar disorders, mania, migraine and chronic or neuropathic pain. Levetiracetam has been produced by a variety of synthetic methods such as those described in, but not limited to, U.S. Pat. No. 4,943,639, GB 2,225,322 and U.S. Pat. No. 6,107,492.

During a wet granulation process, preparation comprises the following steps (1) blending the mixture of Active Pharmaceutical Ingredient (API) and other required pharmaceutically acceptable additives to make a uniform homogenous blend; (2) adding a wetting agent to granulate the uniform blend; (3) drying and sizing the resulting granules to an optimum size suitable for compression; (4) blending the sized granules with the required pharmaceutically acceptable additives/lubricants; and finally (5) compressing the blended granules into tablets.

Unfortunately, during development and processing of the levetiracetam, it has been observed that such processing as described above is quite sensitive, both to the amount of granulation vehicle added as well as with the drying aspect. The API, levetiracetam, in commercially available KEPPRA® tablets, generally comprises about 76% of the tablet weight. Therefore processing of the pharmaceutical blend is highly influenced by the API. For instance, during a completely Dry Granulation or Direct Compression with this compound, hardness is not attainable and the resulting tablets are friable and exhibit poor binding characteristics. Therefore granulation of any sort must involve a wet granulating agent such as water but, the active is hygroscopic and for instance is very soluble in water (104.0 g/100 ml) and therefore the quantity sprayed during mixing in a High Shear Mixer (HSM) is difficult to manage and/or optimize. When too much water is sprayed, the blend can cake and become very pasty. This pasty material then proceeds to harden in a HSM and sometimes halts the machine or impeller from further processing. Also, during the drying stage, these pasty granules will not lift in a Fluid Bed Dryer (FBD) even at maximum air velocity that is measured in Cubic Meter per Hour (CMH), since they are too heavy. As a result, the granulate takes the shape of a bowl and solidifies (into a solid block) in less than two minutes of hot or room temperature drying. Even if an alternative granulation vehicle is used, such as alcohol, and the granules do not get as drastically pasty or hard as observed with water (since the alcohol evaporates in HSM), the drying is still an issue in that the paste remains unable to lift in the FBD.

SUMMARY OF THE INVENTION

According to a first aspect of the present invention, there is provided a combined-step process for manufacturing pharmaceutical compositions. The combined-step process for the preparation of a pharmaceutical comprises wet granulating and simultaneous fluid bed drying of the pharmaceutical blend. During the process, as the pharmaceutical blend granulates it is simultaneously dried preventing it from becoming a paste. The invention thus provides a formulation preparation process characterized by a "combined" Granulation and Fluid Bed Drying process step.

Surprisingly, the problems described herein, whereby the granules of the pharmaceutical blend become drastically pasty or hard and unable to lift in a Fluid Bed Dryer (FBD)

were overcome by the process of the current invention, which provides for both the hardening-by-wet-granulation as well as the drying-condition-state (for proper fluid bed drying to occur) to be simultaneously effective.

According to a second aspect of the present invention there is provided a pharmaceutical composition which has been prepared by a process comprising wet granulation with simultaneous fluid bed drying of the pharmaceutical blend.

According to a third aspect of the present invention there is provided a method of treating or preventing a central nervous system (CNS) disorder, motion sickness, hyperkinesia, hypertonia, convulsive disorders, such as epilepsy, memory disorders, hypoxic or ischemic type aggressions of the CNS, bipolar disorders, mania, migraine and chronic or neuropathic pain comprising administering a pharmaceutical composition comprising levetiracetam and prepared by a process comprising wet granulation with simultaneous fluid bed drying of the pharmaceutical blend.

DETAILED DESCRIPTION OF THE INVENTION

An embodiment of the present invention provides a process for the preparation of a solid oral pharmaceutical formulation of an active pharmaceutical ingredient characterized by simultaneous Wet Granulation and Fluid Bed Drying. The preparation process for a solid oral dosage formulation herein includes fluidizing the active pharmaceutical ingredient and one or more excipient until the inlet temperature within a fluid bed dryer (FBD) reaches a set point. Once at the set point temperature within the FBD a wet granulating agent is applied to the ingredients. The wet granulating agent is administered at a constant spray rate while, simultaneously, the granulating ingredients are dried in the FBD at a constant air velocity for a fixed time to achieve an optimum LOD, Hardness, Friability and Disintegration Time. The granulation process is controlled, in part, by the inlet air volume supplied to the FBD. The remainder of the process comprises milling of the granules through a screen followed by blending and lubricating the final solid oral form.

This preparation process allows the appropriate hardness to be attained while avoiding the aforementioned problems associated with the previous stepwise granulation and drying process. In particular, no agglomerates are observed and the granules are homogeneous.

A preferred embodiment of the present invention provides a preparation process for the solid oral pharmaceutical formulation of levetiracetam characterized by a simultaneous Wet Granulation and Fluid Bed Drying process step.

The preferred process includes fluidization of levetiracetam and its excipients in a fluid bed dryer for a time sufficient to achieve a stable inlet temperature (for example, 30±5° C.) while allowing enough time to achieve a homogeneous mixture before spraying. For example, the fluidization can be for NLT 5 min following the start of the process. The wet granulating agent, for example, water, is administered for a spraying time of approximately 40 min or less. The flow rate is determined based on the spraying time and the batch size. For example, during manufacture of a batch of 120,000 tablets a flow rate of 200-210 g/min was employed and the granulating ingredients were dried in the fluid bed dryer at a constant air velocity of 500-600 cfm for a fixed time with an inlet temperature of approximately 60° C. to achieve tablets having the desired properties. A smaller batch size can be prepared using a lower wet granulation agent flow rate and/or shorter spray time and/or reduced air velocity. By way of example, a smaller batch (less than 4000 tablets) of levetiracetam containing tablets was manufactured using a process according to the present invention in which the wet granulation agent was sprayed at a constant spray rate of 9.5 g/min (25% water). Simultaneously, the granulating ingredients were dried at a constant air velocity or volume of 40-100 CMH (for example, 60-80 CMH) for 3 minutes to achieve a target LOD, Hardness, Friability and Disintegration Time.

The wet granulating agent used in the process can be water, isopropyl alcohol, methanol, ethanol, chloroform, acetonitrile, or any mixture thereof.

In accordance with another aspect of the present invention there is provided a pharmaceutical composition prepared by the method described above. The pharmaceutical composition is any solid dosage form that comprises granules, including, but not limited to tablets and capsules. The pharmaceutical composition of the present invention may also contain one or more additional formulation ingredients that may be selected from a wide variety of excipients known in the pharmaceutical formulation art. According to the desired properties of the pharmaceutical composition, any number of ingredients may be selected, alone or in combination, based upon their known uses in preparing pharmaceutical compositions. Such ingredients include, but are not limited to, diluents, compression aids, disintegrants, lubricants, binders, flavours, flavour enhancers, sweetener and preservatives.

The term "tablet" as used herein is intended to encompass compressed pharmaceutical dosage formulations of all shapes and sizes, whether coated or uncoated. Substances that may be used for coating include but are not limited to hydroxypropylmethylcellulose, hydroxypropylcellulose, titanium oxide, talc, sweeteners, and colorants.

The term "capsule" as used herein is intended to encompass solid pharmaceutical dosage formulations within a capsule, which may be made of gelatin or other conventional encapsulating material.

As would be readily appreciated by a worker skilled in the art, the daily dosage of the active pharmaceutical ingredient administered to a patient can fall within a wide range of concentrations and depends on a variety of factors such as the patient's sex, age, weight and medical condition, as well as on the method of administration. Thus the quantity of active ingredient in the tablet or capsule compositions is at least 0.5% by weight and can be up to 80% by weight with respect to the composition weight.

According to a specific embodiment of the present invention, the pharmaceutical tablet composition comprises levetiracetam.

For the levetiracetam-containing tablet compositions of the present invention, the tablet comprises levetiracetam in the range 50 to 3000 milligrams (mg), preferably in the range 250 to 1500 mg of levetiracetam. Advantageously, the levetiracetam tablets are prepared according to the process described above, such that the tablets have a Friability of <0.8% in 4 minutes, Disintegration time of <15 minutes, LOD of <4% and a Hardness of 6-12 kp (50 mg), 12-17 kp (500 mg) or 12-24 kp (750 mg). The LOD of dried granules employed in the production of the tablets and prepared according to the process described above is advantageously <2%.

Clinical studies on healthy volunteers have shown that levetiracetam is well tolerated at single dose (up to 5,000 g) and repeated doses (1500 mg/day for 14 days). Preliminary data from tolerability studies suggest good tolerability in epileptic patients of doses up to 4000 mg/day. The daily dose can fall within a wide range of dosage units of levetiracetam, and is generally in the range 5 to 70 mg/kilogram (kg). However, it should be understood that the specific doses can be adapted to particular cases depending on the individual requirements, at the physician's discretion.

Levetiracetam can be employed alone or combined with at least one other pharmaceutically active ingredient. Non-limiting examples of the compounds that can be used in combination with levetiracetam are antivirals, antispastics (e.g., baclofen), antiemetics, antimanic mood stabilizing agents, analgesics (e.g., aspirin, ibuprofen, paracetamol), narcotic analgesics, topical anesthetics, opioid analgesics, lithium salts, antidepressants (e.g., mianserin, fluoxetine, trazodone), tricyclic antidepressants (e.g., imipramine, desipramine), anticonvulsants (e.g., valproate, carbamazepine, phenytoin, . . . ), antipsychotics (e.g., risperidone, haloperidol), neuroleptics, benzodiazepines (e.g., diazepam, clonazepam), phenothiazines (e.g., chlorpromazine), calcium channel blockers, amphetamine, clonidine, lidocaine, mexiletine, capsaicin, caffeine, quetiapine, serotonin antagonists, β-blockers, antiarrhythmics, triptans and ergot derivatives.]

When the pharmaceutical composition of present invention contains levetiracetam, the composition is useful for the treatment or prevention of various diseases and disorders. For example, the present invention provides a method for treating or preventing a central nervous system (CNS) disorder, motion sickness, hyperkinesia, hypertonia, convulsive disorders, such as epilepsy, memory disorders, hypoxic or ischemic type aggressions of the CNS, bipolar disorders, mania, migraine and chronic or neuropathic pain comprising administering a pharmaceutical composition comprising levetiracetam and prepared by a process comprising wet granulation with simultaneous fluid bed drying of the pharmaceutical blend.

Commercially available levetiracetam-containing tablets are sold under the name Keppra® (UCB Pharma, Inc.), which are indicated as an adjunctive therapy in the treatment of partial onset seizures in adults with epilepsy. As would be well appreciated by a worker skilled in the art, the pharmaceutical composition of the present invention containing levetiracetam can also be used as an adjunctive therapy in the treatment of partial onset seizures in adults with epilepsy.

Bioavailability studies can be performed, according to standard techniques well known in the field, to confirm the bioavailability of levetiracetam from tablets prepared using the process of the present invention. For example, the bioavailability of the tablets of the present invention can be compared to that of commercially available Keppra® tablets.

The following examples are given for the purpose of illustrating the present invention and should not be considered as limitations on the scope or spirit of the invention.

COMPARATIVE EXAMPLE 1

Levetiracetam Tablets Prepared Using Standard Stepwise Process

A batch of levetiracetam, 250 mg, was prepared using a standard wet granulation process. The standard wet granulation process comprises the following steps (i) a mixture containing active ingredient is blended to make a uniform homogeneous blend; (ii) a wetting agent is added to granulate the uniform blend; (iii) the resulting granules were dried; (iv) the dried granules are blended with the required pharmaceutically acceptable additives lubricants; and (v) the blended granules are compressed into tablets. The process of this examples was used in an attempt to prepare levetiracetam tablets having the following composition:

| Ingredients | mg/tab |
| --- | --- |
| Levetiracetam | 250.00 |
| Povidone | 48.86 |
| Starch | 24.26 |
| Purified water | q.s.* |
| Add-Drys | |
| Colloidal Silica Anhydrous | 1.30 |
| Magnesium stearate | 1.30 |
| TOTAL TABLET WEIGHT (CORE) | 325.73 |

*44.30 g, corresponding to 8% purified water; removed during processing.

The bulk density of the blend before spraying was 0.51 g/ml. The blend was sprayed at a rate of 22.2 g/min and granulated for a total of 2 minutes. Granules were observed to be pasty and adhering to the impeller and to the walls of the container. An additional 2% of water was incorporated and very pasty granules were formed. Extensive high-shear mixing at low impeller and chopper speeds was applied for an additional 2 minutes. The granules began to solidify and melt to form a plastic-like material; this halted the motion of the impeller.

Issues were also encountered during the drying process (at 25±5° C.): after 45 minutes in the fluid bed dryer, the blend solidified and became sticky causing granules to harden and stick to the container.

EXAMPLE 1

| Composition and Process Pathway for Preparing 250 mg Levetiracetam Tablets | |
| --- | --- |
| Ingredients | mg/tab |
| Levetiracetam | 250.00 |
| Pregelatinized Starch 1500 LM | 16.50 |
| Povidone K29/32 | 20.00 |
| Purified water, USP | q.s.* |
| Add-Drys | |
| Aerosil 200 | 0.50 |
| Pregelatinized Starch 1500 LM | 30.20 |
| Avicel PH 102 | 12.00 |
| Magnesium Stearate | 0.80 |
| TOTAL TABLET WEIGHT (CORE) | 330.00 |
| FILM COATING | |
| Opadry** | 10.00 |
| Purified Water, USP*^ | q.s. |
| TOTAL FINAL TABLET WEIGHT | 340.00 |

*322.00 g total, corresponding to 22% H₂O; removed during processing.
**3% weight gain applied.
*^ Removed during processing.

A batch of levetiracetam containing tablets, 250 mg (3720 tablets), was prepared using the following process.

The blend was sprayed with 172.00 g of water during processing and took 24 minutes to reach an LOD of 1.51%. Additional water (150.00 g, 10%) was added for 13 minutes to reach the target LOD of 1.48%. The blend's bulk density was 0.51 g/ml; and the tapped density was 0.60 g/ml. The tablet properties included a hardness value of 12 kp; a friability percentage of 0.49%; a weight of 337 mg total; and a disintegration time of 3-8 minutes.

EXAMPLE 2

| Composition and Process Pathway for Preparing 500 mg Levetiracetam Tablets | |
|---|---|
| Ingredients | mg/tab |
| Levetiracetam | 500.00 |
| Pregelatinized Starch 1500 LM | 33.00 |
| Povidone K29/32 | 40.00 |
| Purified water, USP | q.s.* |
| Add-Drys | |
| Aerosil 200 | 1.00 |
| Pregelatinized Starch 1500 LM | 60.40 |
| Avicel PH 102 | 24.00 |
| Magnesium Stearate | 1.60 |
| TOTAL TABLET WEIGHT (CORE) | 660.00 |
| FILM COATING | |
| Opadry Yellow YS-1-12609** | 20.00 |
| Purified Water, USP*^ | q.s. |
| TOTAL FINAL TABLET WEIGHT | 680.00 |

*401.10 g total, corresponding to 20% $H_2O$; removed during processing.
**3% weight gain applied.
*^Removed during processing.

A batch of levetiracetam containing tablets, 500 mg (3500 tablets), was prepared using the following process.

The blend was sprayed at 8 g/min with 401.10 g of water during processing and took 22 minutes to reach an LOD of 1.75%. No additional spraying was required to reach the target LOD. The yield after FBD granulation was found to be 98.5%; the bulk density was 0.56 g/ml; and the tapped density was 0.66 g/ml. The tablet properties included a hardness value of 19-26 kp; a weight of 678 mg total; and a disintegration time of 7-8 minutes.

EXAMPLE 3

| Composition and Process Pathway for Preparing 750 mg Levetiracetum Tablets | |
|---|---|
| Ingredients | mg/tab |
| Levetiracetam | 750.00 |
| Pregelatinized Starch 1500 LM | 49.50 |
| Povidone K29/32 | 60.00 |
| Purified Water, USP | q.s.* |
| Add-Drys | |
| Aerosil 200 | 1.50 |
| Pregelatinized Starch 1500 LM | 90.60 |
| Avicel PH 102 | 36.00 |
| Magnesium Stearate | 2.40 |
| TOTAL TABLET WEIGHT (CORE) | 990.00 |

| Composition and Process Pathway for Preparing 750 mg Levetiracetum Tablets | |
|---|---|
| Ingredients | mg/tab |
| FILM COATING | |
| Opadry Pink YS-1-14129** | 30.00 |
| Purified Water, USP*^ | q.s. |
| TOTAL FINAL TABLET WEIGHT | 1020.00 |

*384.00 g total, corresponding to 32% $H_2O$; removed during processing.
**3% weight gain applied.
*^Removed during processing.

A batch of levetiracetam containing tablets, 750 mg (1400 tablets), was prepared using the following process.

Tablets were prepared using a similar procedure of Examples 1 and 2. The yield after FBD granulation was found to be 95.8%; the bulk density was 0.565 g/ml; and the tapped density was 0.66 g/ml. The tablet properties included a hardness value of 20 kp; a friability percentage of 0.31%; a weight of 981 mg total; and a disintegration time of 3-6 minutes.

EXAMPLE 4

Scale-Up of Process for Preparing Levetiracetam Tablets

Three batches of 120,000 tablets were prepared using the process of the present invention. The tablets in the three batches contained 250 mg, 500 mg and 750 mg levetiracetam, respectively. The tablets were manufactured to have the final formulation as set out in Table 2.

The three batches were manufactured using a T3 Fluid Bed Dryer. Due to the capacity of the T3 Fluid Bed Dryer, in order to manufacture 120,000 tablets, 2 sublots of Levetiracetam granules were required for the batch of 500 mg tablets and 3 sublots of Levetiracetam granules were required for the batch of 750 mg tablets.

To prepare one sublot of Levetiracetam granules, the following procedure was followed: Levetiracetam (item #1), Pregelatinized Starch (item #2) and Povidone (item #3) were sifted through #14 mesh and added into the T3 Fluid Bed Dryer (FBD) to be preheated and premixed for at least 5 min. Aqueous 14.4% Povidone solution (item #4 dissolved into item #5) was used as granulation agent with post rinsing with purified water (item #6). The wet granulation process was performed in the FBD with a steady fluidization. Air volume at the beginning was set to 500-600 cfm to initiate fluidization and break up lumps if available, and was set constant at the same rate. One spray gun was used to deliver the granulation solution at about 200-210 g/min into the FBD processor on the granules while fluidizing. After depletion of Povidone solution, a rinse solution was used to rinse any residue of Povidone solution. The FBD processor continued drying till LOD of granules was less than 2%. At the end of drying, the Levetiracetam dried granules were discharged and milled through 039R Comill at 1200 rpm.

Final Blending Stage

All the sublots for each strength were combined for the final blending stages. Aerosil (item #7) and Avicel (item #8) were blended for 3 min in a V-blender prior to sifting though 20 mesh screen. The prescreened materials were then added into a bigger blender along with all of the Levetiracetam sublots and mixed for 7 min. Then Magnesium stearate (item #9) was added and mixing continued for additional 3 min.

Compression and Coating Stage

Tablets were compressed to establish a suitable hardness range with passing friability and disintegration limits. For all strengths there were no weight variation or flow problems observed and tablets thickness, hardness and weight show minimal variation during the compression run and appeared within control of set parameters. Tablets were then coated in O'Hara coating pan into different sublots depending on coating pan size. Each strength has a different coating color (items #10-#12).

Tablets from each batch (i.e., at each strength) were tested and found to pass where Q NLT 85% at 30 min (Specification). Actual results at 30 min were: for 250 mg (L# 9003) 99.2% was released; for 500 mg (L# 7893) 99.9% was released; and for 750 mg (L# 9004) 95.7% was released.

The tablets produced using this process were found to exhibit the following characteristics: LOD <2%; Hardness 6-12 kp (250 mg), 12-17 kp (500 mg), 12-24 kp (750 mg); Friability <0.8% in 4 min; and Disintegration time <15 minutes in water.

What is claimed is:

1. A process for the preparation of a solid oral pharmaceutical comprising: (a) wet granulating a pharmaceutical blend comprising a pharmaceutically active ingredient; and (b) simultaneously fluid bed drying the blend, wherein the pharmaceutically active ingredient is levetiracetam, wherein the granules produced are homogeneous and free of agglomerates.

2. The process according to claim 1, wherein the wet granulating is performed using a wet granulating agent.

3. The process according to claim 2, wherein the wet granulating agent is water.

4. The process according to claim 2, wherein the wet granulating agent is sprayed for a spray time of up to about 40 minutes at a spray rate of 200-210 g/min.

5. The process according to claim 2, wherein the wet granulating agent is sprayed at spraying rate in the range of 1-20 g/min.

6. The process according to claim 1, wherein the fluid bed drying employs an air velocity in the range of 500-600 cfm (850-1020 CMH).

TABLE 1

| | | Strength (mg) | | | | |
|---|---|---|---|---|---|---|
| | | 250 (1 sublot) | 500 (2 sublots) # of Tablets | | 750 (3 sublots) | |
| | | 120,000 | 2 × 60,000 | | 3 × 40,000 | |
| Item # | Ingredients | QTY (kg) % | QTY (kg) | % | QTY (kg) | % |
| 1 | Levetiracetam | 30.000   75.8 | 30.000 | 75.8 | 30.000 | 75.8 |
| 2 | Pregelatinized Starch, NF (Starch 1500) | 5.600   14.1 | 5.600 | 14.1 | 5.600 | 14.1 |
| 3 | Povidone K29/32, USP | 1.440   3.6 | 1.440 | 3.6 | 1.440 | 3.6 |
| 4 | Povidone K29/32, USP | 0.960   2.4 | 0.960 | 2.4 | 0.960 | 2.4 |
| 5 | Purified water | 5.700   15.0 | 5.700 | 15.0 | 5.700 | 15.0 |
| 6 | Purified water | 1.900   5.0 | 1.900 | 5.0 | 1.900 | 5.0 |
| | ADD DRYS | | | | | |
| 7 | Colloidal Silicon Dioxide NF (Aerosil) | 0.060   0.2 | 0.060 | 0.2 | 0.060 | 0.2 |
| 8 | Avicel PH 102 (MCC) NF | 1.440   3.6 | 1.440 | 3.6 | 1.440 | 3.6 |
| 9 | Magnesium Stearate non Bovine NF | 0.096   0.2 | 0.096 | 0.2 | 0.096 | 0.2 |
| | Total Tablet Weight (core) | 39.60   12.0 | 39.60 | 12.0 | 39.60 | 12.0 |
| | FILM COATING | | | | | |
| 10 | Opadry Blue YS-1-10749-A | 1.20   3.0 | | | | |
| 11 | Opadry Yellow YS-1-12609 | | 1.20 | 3.0 | | |
| 12 | Opadry Pink YS-1-14129 | | | | 1.20 | 3.0 |
| | Total Final Tablet Weight (on dried basis) | 40.80 | 40.80 | | 40.80 | |

TABLE 2

Composition of Particularly Preferred Embodiment

| Ingredients | mg/tab |
|---|---|
| Levetiracetam | 750.00 |
| Pregelatinized Starch 1500 LM | 49.50 |
| Povidone K29/32 | 60.00 |
| Purified water, USP | q.s.* |
| Add-Drys | |
| Aerosil 200 | 1.50 |
| Pregelatinized Starch 1500 LM | 90.60 |
| Avicel PH 102 | 36.00 |
| Magnesium Stearate | 2.40 |
| TOTAL TABLET WEIGHT (CORE) | 990.00 |

*384.00 g total, corresponding to 32% $H_2O$; removed during processing.

7. The process according to claim 1, wherein the fluid bed drying employs an air velocity in the range of 40-100 CMH.

8. The process according to claim 1, wherein the solid oral pharmaceutical is a tablet or a capsule.

9. The process according to claim 8, wherein the solid oral pharmaceutical is a tablet having an LOD of <4%, a Friability of <0.8% in 4 minutes, and a disintegration time of <15 minutes.

10. The process according to claim 1, wherein said solid oral pharmaceutical is useful for the treatment of a Central Nervous System disorder, motion sickness, hyperkinesia, hypertonia, convulsive disorders, memory disorders, hypoxic or ischemic type aggressions of the CNS, bipolar disorders, mania, migraine and chronic or neuropathic pain.

11. The process according to claim 10, wherein the convulsive disorder is epilepsy.

12. A pharmaceutical composition prepared by a process comprising: (a) wet granulating a pharmaceutical blend comprising a pharmaceutically active ingredient; and (b) simultaneously fluid bed drying the blend, wherein the pharmaceutically active ingredient is levetiracetam, wherein the granules produced are homogeneous and free of agglomerates.

13. The pharmaceutical composition according to claim 12, which is a tablet or a capsule.

14. A method of treating a Central Nervous System disorder, motion sickness, hyperkinesia, hypertonia, convulsive disorders, memory disorders, hypoxic or ischemic type aggressions of the CNS, bipolar disorders, mania, migraine and chronic or neuropathic pain in a patient comprising administering to the patient a pharmaceutical composition prepared by a process comprising: (a) wet granulating a pharmaceutical blend comprising a pharmaceutically active ingredient; and (b) simultaneously fluid bed drying the blend, wherein the pharmaceutically active ingredient is levetiracetam, wherein the granules produced are homogeneous and free of agglomerates.

15. The method according to claim 14, wherein the convulsive disorder is epilepsy.

* * * * *